(12) United States Patent
Wegman et al.

(10) Patent No.: US 7,824,673 B2
(45) Date of Patent: Nov. 2, 2010

(54) REDUCTION OF ADIPOSE TISSUE

(75) Inventors: Edwin H. Wegman, Hewlett Bay Park, NY (US); Burton Bronsther, Hempstead, NY (US); Ellyn Bronsther, legal representative, Hempstead, NY (US)

(73) Assignee: Advance Biofactures Corporation, Lynbrook, NY (US)

( * ) Notice: Subject to any disclaimer, the term of this patent is extended or adjusted under 35 U.S.C. 154(b) by 736 days.

(21) Appl. No.: 11/237,543

(22) Filed: Sep. 28, 2005

(65) Prior Publication Data

US 2006/0177434 A1    Aug. 10, 2006

Related U.S. Application Data

(63) Continuation of application No. 10/172,601, filed on Jun. 14, 2002, now Pat. No. 6,958,150, which is a continuation-in-part of application No. 08/757,904, filed on Nov. 27, 1996, now abandoned, which is a continuation of application No. 08/356,112, filed on Dec. 15, 1994, now abandoned.

(51) Int. Cl.
*A61K 38/43*    (2006.01)
*A61K 38/46*    (2006.01)

(52) U.S. Cl. .................................. 424/94.67; 424/94.1

(58) Field of Classification Search ................ 424/94.1, 424/94.67

See application file for complete search history.

(56) References Cited

U.S. PATENT DOCUMENTS

| 5,393,792 | A | 2/1995 | Stern |
| 5,422,103 | A | 6/1995 | Stern |
| 5,514,370 | A | 5/1996 | Stern |
| 5,589,171 | A | 12/1996 | Wegman |
| 6,086,872 | A | 7/2000 | Wegman |
| RE39,941 | E | 12/2007 | Wegman |
| 2006/0204488 | A1 | 9/2006 | Badalamente |
| 2007/0224183 | A1 | 9/2007 | Sabatino et al. |
| 2007/0224184 | A1 | 9/2007 | Badalemente et al. |

OTHER PUBLICATIONS

Answers.com, Definition "cellulite" accessed by Examiner Sep. 7, 2007.*
MeSH Descriptor Data "Hyaluronoglucosaminidase" http://www.nlm.nih.gov/cgi/mesh/2008/MB_cgi?mode=&term=Hyaluronidase, 1 page only.*
Friedman, K., et al., "Degradation of porcine dermal connective tissue by collagenase and hyaluronidase," British J. of Dermatology, 115:403-408 (1986).

* cited by examiner

*Primary Examiner*—L Blaine Lankford
*Assistant Examiner*—Thane Underdahl
(74) *Attorney, Agent, or Firm*—Elmore Patent Law Group, PC; Carolyn S. Elmore; Mahreen Chaudhry Hoda

(57) ABSTRACT

A simple search was made on the Internet. There were at least a few hundred entries. The following seem to be the best of the few dozen examined. The first page of each is cited below for identification.

8 Claims, No Drawings

REDUCTION OF ADIPOSE TISSUE

RELATED APPLICATIONS

This application is a continuation of Serial No. 10/172,601 filed on Jun. 14, 2002 now U.S. Pat. No. 6,958,150, which is a continuation-in-part of Ser. No. 08/757,904 filed Nov. 27, 1996 now abandoned, which is a continuation of Ser. No. 08/356,112 Dec. 15, 1994 now abandoned.

BACKGROUND OF THE INVENTION

Liposuction (otherwise known as suction lipectomy, suction assisted lipectomy dissection, as well as by other names), is a procedure that mechanically removes fat from the subcutaneous tissues. It has been used primarily in cosmetic surgery to extract adipose tissue at specific areas of the male and female human body. Less common uses of liposuction have been removal of lipoma (benign fatty tumor) and much less commonly it has been used for the removal of unusual fatty tumors. It has also been used as a staged procedure for weight loss with questionable success.

The procedure is carried out by anesthetizing the patient to a varying degree or the area that is to be treated. Small incisions are made at points chosen by the treating physician and a canulla (a long hollow metal tube) having a series of holes along its length is inserted into the subcutaneous adipose tissue. A vacuum of roughly one negative atmosphere is applied and the semi-solid fat is mechanically loosened by the combined forces of the pushing and pulling of the canulla and the vacuum. The loosened fatty tissue is then drawn by vacuum through the canulla and removed from the body Liposuction by mechanical-vacuum means is a very common and desirable procedure performed around the world. However, the mechanical traumatization of the subcutaneous fat caused by this method of removal carries with it significant morbidity and other undesirable post-operative effects including, but not limited to, ecchymosis (black and blue skin), infection, hematoma, prolonged edema, and contour deformity due to uneven removal of fat.

BRIEF SUMMARY OF THE INVENTION

The invention provides a new method to obtain the reduction of what can be considered by patients and physicians to be excess amounts of unaesthetic and/or redundant subcutaneous adipose tissue. When collagenase with or without other proteinase(s) is introduced into subcutaneous adipose tissue of a living animal body, a dissociation and reduction of the adipose tissue at that location occurs. In a single treatment, reduction of the tissue from its original volume may range from 25% to 75% and higher, up to substantially 100%. This effect is of great benefit as previous methods of fat removal involved mechanical traumatization, incisions, and risks of contour deformities and mechanical injuries to tissues adjacent to the adipose tissue.

The method is used to rid the patient of unwanted subcutaneous fat cells without necessity of incisions, without significant trauma to the subcutaneous tissues, and without significant risk of infection as no metal canulla will be repeatedly introduced into the subcutaneous tissues, thus avoiding the risk of introducing with it bacteria from outside into the wound. Also eliminated is the possibility of mechanical damage to important anatomical structures adjacent to the area of liposuction by inadvertent misplaced canulla thrust. Post-operative ecchymosis may be lessened as well as the post-operative edema due to mechanical disruption.

While reduction of subcutaneous fat is the principal objective of the invention, the treatment may also be applied to adipose tissue elsewhere in the body.

The foregoing discussion and that following the heading "Detailed Description" is largely directed to application of the invention for reduction of excess subcutaneous adipose tissue considered to be unaesthetic and/or redundant. The invention is likewise applicable to the reduction and removal of lipomas, whether found at the surface of the skin, within the skin, subcutaneous, or anywhere else in the body.

Lipomas are tumors of fatty tissues, generally benign. If malignant, they are known as liposarcomas. Benign lipomas contain normal fat that is encapsulated within a fibrous sphere, thus often compressing the fat and causing it to feel more firm than surrounding fat. Many lipomas are asymptomatic and are removed for non-medical reasons. However, a significant number of them cause the patient pain or discomfort and they interfere with normal activity.

At present, lipomas are usually treated in one of the following ways: 1) wide excision with large dissection, 2) limited incision with limited dissection, or 3) liposuction.

If a large excision is performed, there is the problem of a very large scar and the accompanying issues of healing such a scar. In addition, removing a large mass from the subcutaneous tissues will leave behind a potential space which can fill with blood resulting in hematoma followed by consolidation of the hematoma and the remnants of a mass of scar tissue. This may be more problematic than the original lipoma.

Liposuction of a lipoma requires a smaller incision, therefore results in a smaller scar and carries a smaller risk of infection. However, the potential for hematoma formation, followed by scar mass residual, remains an issue of concern.

The present invention avoids these problems by introducing into lipoma(s) effective amounts of collagenase or collagenase plus another proteinase.

The invention may be used for the treatment of lipomas and other adipose tissues in humans and in animals, including dogs, cats, birds, and other comfort animals, horses, swine, sheep, and other farm animals, laboratory animals, and wild animals both in their natural state and in zoos.

DETAILED DESCRIPTION

In the human body, a more or less continuous layer of adipose tissue, composed largely of fat cells, underlies the skin. This subcutaneous fat not only varies in thickness from place to place in the body but also from individual to individual. Usually for cosmetic reasons, it may be desirable to reduce the amount of subcutaneous fat at selected locations.

The present invention accomplishes this by introducing into the tissue effective amounts of collagenase or collagenase plus at least one other proteinase. The said other proteinase may be chosen from any of the four recognized classes of proteinases, viz. the cysteine serine, aspartic and metallo proteinases. Of these, a cysteine proteinase is preferred, and especially clostripain. A serine proteinase such as trypsin or chymotrypsin is also preferred.

The collagenase and other proteinase(s) can be separately introduced, though it is generally more convenient that they both be in a single solution. It is within the skill of the art to select carriers that are pharmaceutically acceptable, including inertness towards the collagenase and other proteinase(s). Examples are normal saline, aqueous dextran solution, aqueous hetastarch solution, preferably suitably buffered. In some instances the physician may prefer a slow release liquid or solid carrier formulation for injection or implantation, in which case the collagenase dosage would usually be somewhat higher than that used in a simple aqueous injection. One can use as carrier fibrin glue, comprising fibrin or fibrin precursors, e.g. fibrinogen plus thrombin; see U.S. Pat. No. 5,279,825. Again, selection of carrier and methods of preparing formulations are within the skill of the art. Though water is necessary to activate the enzymes, the aqueous interstitial fluid present in the subcutaneous tissues is sufficient to do this.

The physician will first select what location(s) in the body she/he wishes to treat. In order to limit the amount of enzymes (collagenase and other proteinase) introduced into the body at one time and to permit a preliminary evaluation of results, a limited area—which may be less than the total area—may be chosen for initial treatment. The treatment solution is injected percutaneously into the subcutaneous adipose tissues, preceded if the physician or patient so desires with a light local anesthesia.

For maximum effect from a given quantity of the enzyme solution it should be injected in small quantities at a multiplicity of closely spaced points in the area, preferably spaced not more than about two centimeters apart and even much closer.

The physician will estimate the amount of adipose tissue underlying the area to be injected. Dosage usually may range from about 5 or less to about 150 or 500 or more or in some cases as much as 3500 or more ABC units of collagenase per gram of adipose tissue treated. Amounts from about 10 to about 100 ABC units per gram are often preferred.

Dosage of other proteinase(s) may range from none to about 350 or more FFC units proteinase activity per gram of adipose tissue.

Collagenase is an enzyme that has the specific ability to digest collagen. It is derived commercially from fermentation by *Clostridium histolyticum*, and is purified by a chromatographic technique. The potency assay of collagenase is based on the digestion of undenatured collagen (from bovine tendon) at pH 7.2 and 370° C. for 20-24 hours. the number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Concentrations of enzymes in the pharmaceutically acceptable carrier are chosen on the principle that sufficient liquid is present to diffuse adequately in the subcutaneous fatty tissue yet no more than adequate to carry the desired amount of actives into the area under treatment. A range from about 50 to 5,000 ABC units collagenase per mL is suitable and considerable latitude within and beyond this range is possible in making the choice for a given situation. Similarly, considerable latitude can be used in choosing the concentration of other proteinase(s), though they will often fall within the scope of 1 to 10,000 FFC units per mL.

Since diffusion into the adipose tissue and the freeing of fat therefrom is seldom complete, it is often desirable to repeat the treatment at least once. This can be done after a few days, say one week.

This invention usually results in significant reduction of adipose tissue within 24 hours. Residue from the adipose tissue in the treated location is at least partly metabolized. If desired, freed fat, cell debris and free cells still present at the location after one or two days may be suctioned off.

Although the invention is intended to be a substitute for liposuction, it may also be used as an adjunct to it. In such case the treatment is directed to sufficient disruption of the adipose tissue to make it easier to remove by suction. The liposuction stage will follow the application of the invention by one to three days.

Lipomas are normally removed by surgery or liposuction. By use of collagenase or collagenase plus one or more other proteinases as described herein, the lipomatous tumor can be completely removed. The procedures, carriers, dosages and concentrations described above are applicable to the treatment of lipomas. Likewise, as described herein, collagenase essentially free from other proteinases or collagenase plus other proteinases may be used. Fat released from the lipoma is metabolized.

EXPERIMENTAL

A series of experiments was carried out to observe the effect, if any, of injecting different concentrations of collagenase plus proteinase into the fat pads of mature male Zucker rats.

It was generally observed that a dose of between about 250 to about 1,000 ABC units of collagenase per fat pad when injected percutaneously caused moderate to severe tissue disruption in 24 hours. The surgeons who autopsied the rats commented that hemorrhage and trauma were significantly less at all dosage levels than the effect typically observed following mechanical liposuction. It was observed that as the dose was increased, the amount of interstitial hemorrhage tended to increase. Dosages of 2,000 ABC units and higher resulted in considerable local hemorrhage, but at dosages of 500 to 1,000 ABC units hemorrhage was of a generally moderate character. In this regard, it may be mentioned that in typical liposuction the amount of blood is about 25% of the fat removed.

Histopathological analysis of organs of rats treated with the collagenase-plus-proteinase material containing 1,000 and 2,000 ABC units of collagenase reveals normal tissue architecture and cell morphology with no histologic lesions.

It was observed that multi-site percutaneous injection resulted in better fat disruption than single site injection. It was also noted that when the enzyme was slowly infused into the fat pad and the infusion needle moved as the enzyme was being injected, severe interstitial hemorrhage was observed, along with good to moderate fat disruption, when the animal was sacrificed in 24 hours. However, animals sacrificed at a later date showed no signs of hemorrhage, and there was a moderate disruption of the fat pad.

Animal Model

Zucker rat, male.

Autopsy Criteria

Grade O—No tissue disruption

Grade I—Mild tissue disruption, mild hemorrhage/necrosis

Grade II—Moderate tissue disruption, mild hemorrhage/necrosis

Grade III—Severe tissue disruption, hemorrhage/necrosis

Grade IV—Complete tissue disruption, hemorrhage/necrosis

Collagenase-Plus-Proteinase Material Used

ABC units collagenase per gram: 990,000

FFC units proteinase activity per gram: 24,700

Solvent: sterile normal saline
  Anesthesia
3 mL Rompum (xylazine) and 7 mL Ketamine HCl
Use 0.1 mL per 100 gm animal weight
Inject IP
(Experiments H and I below, done without anesthesia, established that collagenase and collagenase plus another proteinase, not the anesthesia are the active agents).
  Procedure
  The rats were anesthetized by intraperitoneal injection. With each rat, one fat pad was injected with normal saline as control and three others were injected with the solution being tested.

Experiment A

No. of rats: Three Zuckers
Test solutions: 500 ABC u in 5 mL saline 1,000 ABC u in 6 mL saline 22 gauge, 8" needle used
Injections: Solutions slowly infused into fat pad, moving needle. 12:00 PM day 1
Results: Rat #1 autopsied 10:45 AM day 2
  Site 1: saline: Normal fat pad
  Site 2: 500 u. Total disruption of fat pad with interstitial bleeding. 20% of fat pad digested to a depth of 50% but not down to dermis.
  Site 3: 500 u—same as site 2 with considerably more interstitial bleeding.
  Site 4: 500 u—same as sites 2 and 3 with more interstitial bleeding—fat more disrupted, with no single area reaching the dermis. Considerable amount of oily substance observed in the injected sites which would reflect a reduction or disruption of fat cells and possibly a reduction in the size of the fat pads in all of the above
Rat #3—Autopsied day 5
  Site 1: Saline: Normal fat pad.
  Site 2: 1,000 u in 6 mL. No hemorrhage, no necrosis, modest tissue degradation.
Thinning of fat grade II and III, 40% adipolysis.
  Site 3: 1,000 u. Mild adipose tissue degradation, no hemorrhage, grade I.
  Site 4: 1,000 u. Full thickness digestion of ½ of fat pad. Free fat floating over tissue, no hemorrhage, no necrosis, grade III.
Rat #2 Autopsied day 4
  Site 1 control: Normal
  Site 2: 500 u, Grade I
  Site 4: 500 u, Grade II
  Site 3: 500 u, Grade III
Summary/Observation: In three days there is no sign of hemorrhage in all animals. Moderate to good amount of adipose tissue disruption. In 24 hours, there is no interstitial bleeding with a moderate amount of fatty tissue disruption. interstitial bleeding.
Summary/Observation: Percutaneous injection at multiple points causes less trauma hemorrhage than perfusion from a needle moving through the fat pad. It seems that digestion of the fat pad is considerable using this technique.

Experiment C

No. of rats: One Zucker
Test solution: 2,000 ABC u in 0.5 mL saline
Method: Injected (12:15 PM—day 1) percutaneous into each pad in 0.1 mL aliquots (5 places). Saline control was done in the same manner.
Results: Autopsied 9:00 AM day 2.
  Site 1: Saline: Normal fat pad.
  Sites 2-4: Digestion grade III down to dermis. Complete disruption of fat pads.
Summary/Observation: There was good disruption of pad with significant bleeding. Should be repeated at a lower dose.

Experiment D

No. of rats: Two Zuckers
Test solutions: 500 ABC u in 0.5 mL and 1,000 ABC u in 0.5 mL of saline
Method: Rat #1: 0.5 mL containing 1,000 u was injected percutaneous into each fat pad in 0.1 mL aliquots. 0.5 mL of saline was injected as a control.
  Rat #2: Repeated on Rat #2 using 500 u/0.5 mL.
  Rats injected day 1.
Results: Rats autopsied day 2.
  Rat #1: Grade IV on all three test sites. Considerable hemorrhage in areas of muscle and fascia upper left and lower right.
  Rat #2: Grade III on all three sites, moderate hemorrhage.
Summary/Observation: 500 units seems to give good adipose tissue dissolution without the massive hemorrhage that was observed with 1,000 units.

Experiment E

No. of rats: One Zucker
Test solution: 1,000 ABC u in 0.5 mL saline
Method: 0.5 mL containing 1,000 u was injected percutaneous in 0.1 mL amounts into three fat pads. A fourth pad was injected with control saline.
Results: The fat pads were dissected out and weighed.
  Control site upper LF—12.1 gm.
  Test site upper RT—7.1 gm.
  Test site lower RT—9.1 gm.
  Test site lower LF—9.9 gm.
Summary/observation: At this dosage, the fat pads lost, respectively, 41%, 25% and 18% of the weight of the control pad; average loss was 28%. Based on a one sider "T" test there was a significant statistical difference between the control and test sites.

Experiment F

No. of rats: Two Zuckers
Test solution: 250 ABC u in 0.5 mL saline
Method: 250 u in 0.5 mL saline injected percutaneous in 0.1 mL increments in each of three sites per animal. A fourth site is used as a saline control.
Results: Rat #1: Sacrificed day 3
  Upper left test—Grade II and III
  Lower right test—Grade II and III
  Lower left test—Grade 0 and II
  Control—Normal
  Rat #2: Sacrificed day 4
    Upper right test—Grade I and II
    Lower right test—Grade 0 and I
    Upper left test—Grade 0
    Lower left control—Grade 0

Summary/Observation: Adipolysis at the 250 u level does not seem as effective when compared to the higher levels in other experiments.

Experiment G

No. or rats: Three Zuckers
Test solutions: 250 ABC u/0.5 mL, 500 ABC u/0.5 mL, 1,000 ABC u/0.5 mL
Method: All four fat pads of each rat were injected percutaneous with one concentration.
Result: Rat 1: 250 u/0.5 mL
  Site 1: Grades II and III.
    Hemorrhage light.
  Site 2: Grade II.
    Hemorrhage moderate.
  Site 3: Grades II and III.
    Hemorrhage light.
  Site 4: Grade II. Hemorrhage—0.
Rat 2: 500 u/0.5 mL.
  Site 1: Grade III.
    Hemorrhage light.
  Site 2: Grade IV.
    Hemorrhage moderate, oily.
  Site 3: Grade IV.
    Hemorrhage moderate.
  Site 4: Grades II and III.
    0 Hemorrhage.
Rat 3: 1,000 u/0.5 mL
  Site 1: Grade IV.
    Heavy hemorrhage.
  Site 2: Grade III and IV.
    Moderate hemorrhage.
  Site 3: Grade III.
    Heavy hemorrhage.
  Site 4: Grade III.
    0 Hemorrhage.
  Oily substance over all sites.
Summary/Observation: In this experiment there was no significant different in adipolysis between 1,000 u and 500 u. Hemorrhage seems to be slightly heavier in the 1,000 u.

Experiment H

Objective
  To determine the effect of highly purified collagenase on the subcutaneous fat pads of rats.
Materials and Methods
  (1) Collagenase: Nucleolysin®, which is a collagenase purified by a chromatographic technique and essentially free from other proteinases, available from Advance Biofactures Corp., Lynbrook, N.Y. 11563.
  (2) Diluent: The lyophilized Nucleolysin® was re-constituted in a diluent consisting of water for injection USP, sodium chloride and calcium chloride. Each mL of reconstitution Diluent contained 9.0 mg NaCl USP and 0.297 mg $CaCl_2$ USP.
  (3) Six female Zucker rats.
  (4) The four subcutaneous fat pads were designated: a=right anterior, b=left anterior, c=right posterior, d=left posterior.
  (5) To avoid the possibility that administration of pain killers might interfere with the results, and in view of the short term nature of the experiment, no anaesthesia was used.
  (6) Each of the four subcutaneous fat pads of each rat was injected with either 250 ABC units collagenase in the form of Nucleolysin® dissolved in 0.2 mL Diluent (T), or with 0.2 mL Diluent only (P) according to the following schedule.

|        | Pad a | Pad b | Pad c | Pad d |
|--------|-------|-------|-------|-------|
| Rat #1 | P     | P     | T     | T     |
| Rat #2 | T     | T     | P     | P     |
| Rat #3 | P     | T     | P     | T     |
| Rat #4 | T     | P     | T     | P     |
| Rat #5 | P     | T     | T     | P     |
| Rat #6 | T     | P     | P     | T     |

(7) Twenty-four hours after injection all six rats were sacrificed at the same time in a $CO_2$ chamber.

Analysis and Interpretation of Results
  Table 1 gives the weights of the rats before injection and before sacrifice. All of the animals appeared normal during the course of the experiment; there were no outward signs of pain.
  After the rats were sacrificed, they were all incised to reveal the fat pads. A scale of 0 to 9 was used to describe the amount of disruption of the fat pads. An assigned value of 0 meant that no disruption was observed; an assignment of 9 was given to the fat pad(s) showing the most disruption (relative to the other fat pads). The assignment of a value to each fat pad was achieved through a consensus reached between two investigators neither of whom was aware of which injection was received by each fat pad. The results are given in Table 2.
  Note that all of the fat pads that received an injection of Diluent only were rated 0, whereas the pads that received an injection of Nucleolysin® received ratings of 2 to 9. These results are highly significant, and the Mann-Whitney test indicates there is a significant difference between a diluent injection and a Nucleolysin® injection at the 99% degree of confidence.

TABLE 1

Weights of the Zucker Rats

| Rat | weight before injection, g | weight before sacrifice, g | weight difference, g |
|-----|---------------------------|---------------------------|---------------------|
| #1  | 383.5                     | 383.3                     | −0.2                |
| #2  | 273.8                     | 276.1                     | +2.8                |
| #3  | 301.9                     | 307.8                     | +5.9                |
| #4  | 406.0                     | 401.5                     | −4.5                |
| #5  | 380.1                     | 385.8                     | +5.7                |
| #6  | 355.6                     | 357.9                     | +2.3                |
| avg | 350.2                     | 352.1                     | +1.9                |

TABLE 2

Summary of Disruption of Fat Pads

|     | Pad a | | Pad b | | Pad c | | Pad d | |
|-----|-------|--------|-------|--------|-------|--------|-------|--------|
| Rat | Inj.  | Result | Inj.  | Result | Inj.  | Result | Inj.  | Result |
| #1  | P     | 0      | P     | 0      | T     | 8      | T     | 4      |
| #2  | T     | 9      | T     | 3      | P     | 0      | P     | 0      |
| #3  | P     | 0      | T     | 7      | P     | 0      | T     | 5      |
| #4  | T     | 5      | P     | 0      | T     | 5      | P     | 0      |
| #5  | P     | 0      | T     | 8      | T     | 8      | P     | 0      |
| #6  | T     | 2      | P     | 0      | P     | 0      | T     | 2      |

Experiment I

Objective

To determine whether highly purified collagenase, and collagenase containing other proteinase, have different effects on the subcutaneous fat pads of rats.

Materials and Methods (1) Purified collagenase: Nucleolysin®, as described in Experiment H.

(2) Collagenase containing other proteinase: Collagenase having an activity of 202 ABC units collagenase per mg and 436 FFC units other proteinase per mg.

(3) Diluent: Lyophilized (1) and (2) were reconstituted in a diluent consisting of water for injection USP, sodium chloride and calcium chloride. Each mL of reconstitution Diluent contained 9.0 mg NaCl USP and 0.294 mg $CaCl_2$ USP.

(4) Six female Zucker rats.

(5) The four subcutaneous fat pads of each rat were designated as in Experiment H.

(6) No anesthesia was used, for the reasons stated in Experiment H.

(7) Each of the four subcutaneous fat pads of each rat was injected with either 94 ABC units collagenase in the form of Nucleolysin® dissolved in 0.2 mL of Diluent (N) or with 93 ABC units collagenase plus 201 FFC units other proteinase dissolved in 0.2 mL of Diluent (C) according to the following schedule.

|  | Pad a | Pad b | Pad c | Pad d |
| --- | --- | --- | --- | --- |
| Rat #1 | C | C | N | N |
| Rat #2 | N | N | C | C |
| Rat #3 | C | N | C | N |
| Rat #4 | N | C | N | C |
| Rat #5 | C | N | N | C |
| Rat #6 | N | C | C | N |

(8) Twenty two-and-one-half hours after injection all six rats were sacrificed at the same time in a $CO_2$ chamber.

Analysis and Interpretation of Results

Table 1 gives the weights of the rats before injection and before sacrifice. All of the animals appeared normal during the course of the experiment; there were no outward signs of pain.

After the rats were sacrificed, they were all incised to reveal the fat pads. The same two investigators who evaluted the fat pads in Experiment H applied the same scale that was used in that study to the evaluation of the fat pads in this study. The results are given in Table 2.

The Mann-Whitney statistical test indicates there was a significantly greater disruption in the fat pads that received purified collagenase than in those that received collagenase, plus other proteinase (99.5% degree of confidence). [In comparing the present results with the results obtained in Experiment H, there was no significant difference between the fat pads that received 250 ABC units of purified collagenase and the present fat pads that received 94 ABC units (95% degree of confidence.]

The weight of the incised fat pads are given in Table 3, along with its weight as a percentage of the rat's total body weight before sacrifice. A two-way analysis of variance (ANOVA) revealed no significant difference ($\alpha=0.05$) in the weight of the fat pads (as a percentage of total body weight) as a function of fat pad location and injected sample; however, one-way ANOVA revealed a significant difference between the weights of anterior vs. posterior fat pads (although there was no significant difference between the two treatments or between right vs. left fat pads). There was also no significant correlation between the weight of the fat pad and its "disruption value" shown in Table 2.

TABLE 1

Weights of the Zucker Rats

| Rat | weight before injection, g | weight before sacrifice, g | weight difference, g |
| --- | --- | --- | --- |
| #1 | 432.9 | 436.1 | +3.2 |
| #2 | 491.2 | 494.3 | +3.1 |
| #3 | 372.2 | 372.0 | −0.2 |
| #4 | 416.1 | 419.1 | +3.0 |
| #5 | 336.1 | 336.5 | +0.4 |
| #6 | 396.5 | 398.3 | +1.8 |
| avg | 407.5 | 409.4 | +1.9 |

TABLE 2

Summary of Disruption of Fat Pads

|  | Pad a | | Pad b | | Pad c | | Pad d | |
| --- | --- | --- | --- | --- | --- | --- | --- | --- |
| Rat | Inj. | Result | Inj. | Result | Inj. | Result | Inj. | Result |
| #1 | C | 2 | C | 1 | N | 2 | N | 5 |
| #2 | N | 6 | N | 6 | C | 1 | C | 0+ |
| #3 | C | 5 | N | 7 | C | 2 | N | 3 |
| #4 | N | 0+ | C | 0+ | N | 6 | C | 3 |
| #5 | C | 0 | N | 6 | N | 5 | C | 3 |
| #6 | N | 7 | C | 2 | C | 2 | N | 7 |

TABLE 3

Weights of Fat Pads

|  | Pad a | | Pad b | | Pad c | | Pad d | |
| --- | --- | --- | --- | --- | --- | --- | --- | --- |
| Rat | g | % | g | % | g | % | g | % |
| #1 | 5.5 | 1.3 | 9.3 | 2.1 | 8.1 | 1.9 | 9.4 | 2.2 |
| #2 | 10.4 | 2.1 | 8.8 | 1.8 | 13.5 | 2.7 | 11.6 | 2.3 |
| #3 | 8.0 | 2.2 | 9.1 | 2.4 | 9.5 | 2.6 | 8.6 | 2.3 |
| #4 | 7.8 | 1.9 | 10.0 | 2.4 | 10.8 | 2.6 | 10.5 | 2.5 |
| #5 | 7.8 | 2.3 | 6.9 | 2.1 | 8.0 | 2.4 | 9.1 | 2.7 |
| #6 | 8.0 | 2.0 | 12.2 | 3.1 | 10.3 | 2.6 | 10.4 | 2.6 |
| avg | 7.9 | 2.0 | 9.4 | 2.3 | 10.3 | 2.5 | 9.9 | 2.4 |

Collagenase Toxicity Study in Rats

Objective

To observe the effect of daily injections of different concentrations of collagenase/proteinase solutions into the fat pads of Wistar rats.

Materials 1. 6 adult Wistar rats—3 male, 3 female, fed ad libitum

2. Collagenase/proteinase material: 990,000 ABC units collagenase and 24,700 FFC units proteinase activity.

Solutions of 1,000 ABC units in 0.4 mL saline and 2,000 ABC units in 0.4 mL saline.

3. Sterile normal saline.

4. Acepromazine, 2 mg/cc

Procedure

The rats are tranquilized by injecting 1.0 cc/Kg of a solution of Acepromazine subcutaneously. The animals appear tranquilized in about five minutes. The rats are treated as follows: Using a 1,000 units in 0.4 mL saline solution, 0.1 mL is injected percutaneously into each of axillary and hind leg fat pads. This is done for one male and one female rat. This procedure is repeated with a 2,000 units in 0.4 mL solution using another male and female rat. Two control animals are injected using 0.1 mL of saline into each of the areas. This procedure is done daily for a period of fourteen days. The rats are weighed daily. At the end of the test period the animals are sacrificed and autopsied. Sections of the spleen, liver, lungs, pancreas and kidney are sent for histopathology.

Necropsy Observation

Controls: Fat pads intact. All organs normal.
1,000 units: Slight digestion of fat pads, some oil.
No hemorrhage. All organs normal.
2,000 units: Slight to moderate digestion of fat pads.
Yellowing of abdominal wall at site of injection.
All organs normal.

Conclusion

Daily percutaneous injections in the fat pads of mature Wistar rats with solutions containing 1,000 and 2,000 ABC units of collagenase, respectively, have no deleterious effect on the animal. All the rats gained weight. All organs appear grossly normal. Sections of lungs, liver, spleen, pancreas and kidney were sent to histopathology.

Histopathology Report

Both control and test tissue sections exhibit normal tissue architecture and cell morphology. No histologic lesions.

Experiment J

Four human patients suffering from lipoma of the skin were treated with collagenase.

The collagenase was purified by chromatographic techniques so as to be substantially free from other proteinases. It was supplied in lyophilized vials containing 2,200 ABC units of collagenase and sterile diluent.

Each vial was reconstituted in 1.1 mL of sterile diluent consisting of 0.9% sodium chloride and 2 mM calcium chloride for a concentration of 2,000 ABC units per mL.

Dosage was 1,000 ABC units collagenase per centimeter of diameter of the lipoma.

Patient 1

This 57-year-old female patient was diagnosed with a 3 cm by 4 cm×0.5 cm lipoma located on her left anterior thigh. This patient has an unremarkable past medical history and was not taking any concomitant medications. Upon injection of the collagenase, she experienced adverse events of swelling, bruising and tenderness with the lipoma volume remaining static on the 1st and 3rd days post-injection. On the 7th day post-injection, the lipoma volume had decreased by 20% followed by an additional 20% decrease by the 14th day post-injection. By one month post-injection, the lipoma volume had decreased by 100% with no increase/change in volume apparent at the 6th month post-injection visit.

Patient 2

This 34-year-old female patient was diagnosed with a 1 cm×1 cm×0.5 cm lipoma located on her right lower arm. This patient has an unremarkable past medical history and was not taking any concomitant medications. Upon injection of the collagenase, she experienced adverse events of swelling, bruising and tenderness with an increase in the lipoma volume to 1.3 cm×1.3 cm×0.6 cm on the 1st and 3rd days post-injection. On the 7th day post-injection, the lipoma volume had decreased and was essentially static (as compared to baseline) and remained so at the 14th day post-injection. By one month post-injection, the lipoma volume had decreased by 50%; and by three months post-injection, the lipoma volume had decreased by 100% with no increase/change in volume apparent at the 6th month post-injection visit.

Patient 3

This 40-year-old female patient was diagnosed with a 5 cm×5 cm×1.5 cm lipoma located on her left upper arm. This patient has a past medical history significant for hypercholesterolemia, asthma, herniated disc, laryngitis and allergies to cats; however, she was not taking any concomitant medications. Upon injection of the collagenase, she experienced adverse events of swelling, bruising and tenderness with an increase in the lipoma volume to 5.5 cm×5.5 cm×1.5 cm on the 1st and 3rd days post-injection. On the 7th day post-injection, the lipoma volume had decreased and was essentially static (as compared to baseline) with a slight decrease (10%) at the 14th day post-injection. By one month post-injection, the lipoma volume had decreased by 100% with no increase/change in volume apparent at the 6th month post-injection visit.

Patient 4

This 66-year-old male patient was diagnosed with a 1 cm×1 cm×0.5 cm lipoma located on his right distal forearm. This patient has a past medical history significant for obesity, multiple skin nodules (neurofibromatosis) as well as an increased PSA level (biopsy results were negative); and he was taking multivitamins and aspirin as concomitant medications. Upon injection of the collagenase, he experienced adverse events of swelling and tenderness with an increase in the lipoma volume to 1.2 cm×1.2 cm×0.5 cm on the 1st day post-injection. On the 3rd and 7th days post-injection, the lipoma volume was static. Whereas on the 14th day post-injection, the lipoma volume had decreased slightly by 20%. No further reduction in lipoma volume was noted with this patient. The Principal Investigator feels that this was due to the nature of his lipoma—a fibrous/multi-lobulated one that due to the presence of extensive scar tissue is resistant to the effects of the collagenase.

The principal investigator noted that patients 1, 2 and 3 were very pleased with the results of their participation in the study. He also noted the fact that patients that present with fibrous/multi-lobulated lipomas, as in the case of patient 4, are not good candidates for the study due to the extensive scar tissue associated with their lipoma that is resistant to the effects of the collagenase.

The invention claimed is:

1. A method of reducing the amount of adipose tissue at a selected location in the body comprising introducing into said tissue effective amounts of purified collagenase in the substantial absence of another proteinase, wherein said adipose tissue is a lipoma.

2. A method according to claim 1 wherein said lipoma is reduced by substantially 100%.

3. A method according to claim 1 wherein the collagenase is introduced into said lipoma in the amount of from about 250 to about 1,500 ABC units collagenase per centimeter of diameter of the lipoma.

4. A method according to claim 1 wherein the collagenase is introduced into said lipoma in a concentration of from about 50 to about 5,000 ABC units per mL.

5. A method according to claim 1 wherein the collagenase is injected in a liquid pharmaceutically acceptable carrier in a concentration of at least 1,000 ABC units per mL.

6. A method according to claim 1 wherein the collagenase is injected in a liquid pharmaceutically acceptable carrier in a concentration of at least 2,000 ABC units per mL.

7. A method comprising the steps of injecting subcutaneously into a lipoma purified collagenase in a liquid pharmaceutically acceptable carrier, said collagenase being substantially free of other proteinases, in an amount of from about 250 to about 1,500 ABC units collagenase per centimeter of diameter of the lipoma, and in a concentration of from about 50 to about 5,000 ABC units per mL.

8. A method according to claim 1 wherein the collagenase is introduced into said lipoma in a concentration of at least 3500 ABC units per mL.

* * * * *